United States Patent [19]

Kurihashi

[11] Patent Number: 5,437,625
[45] Date of Patent: Aug. 1, 1995

[54] APPARATUS FOR INTUBATION OF LACRIMAL DRAINAGE PATHWAY

[76] Inventor: Katsuaki Kurihashi, 1366-1 Hatsuoi-cho, Hamamatsu-cho, Shizuoka-ken, Japan

[21] Appl. No.: 4,589

[22] Filed: Jan. 14, 1993

[30] Foreign Application Priority Data

Apr. 6, 1992 [JP] Japan .................................. 4-129254
Nov. 12, 1992 [JP] Japan .................................. 4-349676

[51] Int. Cl.$^6$ ............................................ A61M 5/00
[52] U.S. Cl. ........................................ 604/8; 128/898
[58] Field of Search ...................... 604/8–10, 604/28, 49, 285; 401/49; 128/898

[56] References Cited

U.S. PATENT DOCUMENTS

| 2,011,270 | 8/1935 | Chesler | 401/49 |
| 4,305,395 | 12/1987 | Martinez | 604/28 |
| 4,380,239 | 4/1987 | Crawford | 604/28 |
| 4,658,816 | 4/1987 | Ector, Jr. | 604/8 |
| 4,790,810 | 12/1988 | Pugh et al. | 604/8 |

FOREIGN PATENT DOCUMENTS 56-50579 11/1981 Japan .
1531210 9/1977 United Kingdom .

OTHER PUBLICATIONS

Translation of "Direct Silicone Intubation for Reconstruction of Lacrimal Drainage" Kurihashi, Mass. 1992.
"A New Bicanicular Silicone Intubation . . . ", 10th Meeting Esoprs, 8–10 Sep. 1992.
"Bicanalicular Silicone Intubation". . . , Ophthalmologica 876 FR BW Sep. 2, 1992.
Direct Silicone Intubation, Kurihashi, Jun. 1992 New Probe for the Intubation of Lacrimal . . . , Brit. J. Ophthal (1967) 51, 198.
International Ophthalmology 415:411–416, 1991.
Ophthalmologica 1991; 201:1–7, Anatomical, Consideration for Dacryocystorhinostomy.
Lacrimal Surgery, John V. Lindberg (ed) 1988, pp. 109–123.
Lacrimal Surgery, 1988, pp. 241–262.

Primary Examiner—Randall L. Green
Assistant Examiner—Rob Clarke
Attorney, Agent, or Firm—Lorusso & Loud

[57] ABSTRACT

An apparatus for the treatment of the lacrimal duct in which both ends of a thinner and softer tube or rod 0.5–0.7 mm OD and 20–40 mm in length are connected with thicker and harder tubes (0.9–1.2 mm OD and 15–50 mm in length), resulting in a total length of 50–120 mm. Both ends (2 mm) are sealed by silicone to make the closed end and then formed sharp pointed in conical shape.

13 Claims, 5 Drawing Sheets

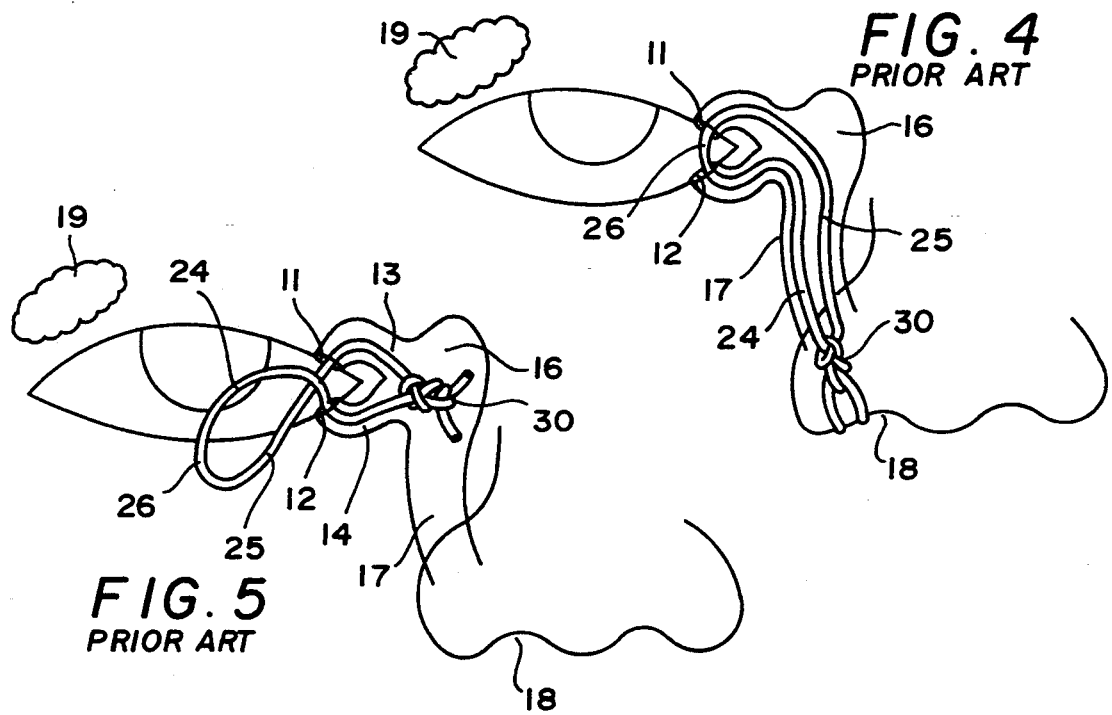
FIG. 4 PRIOR ART
FIG. 5 PRIOR ART
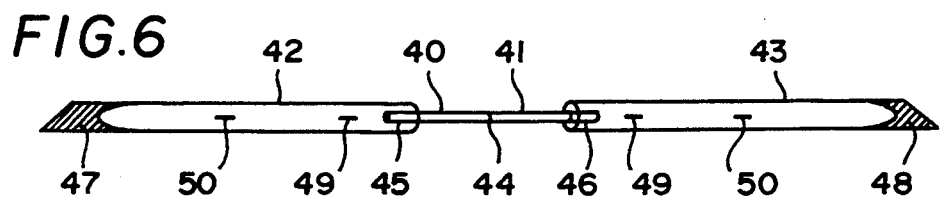
FIG. 6
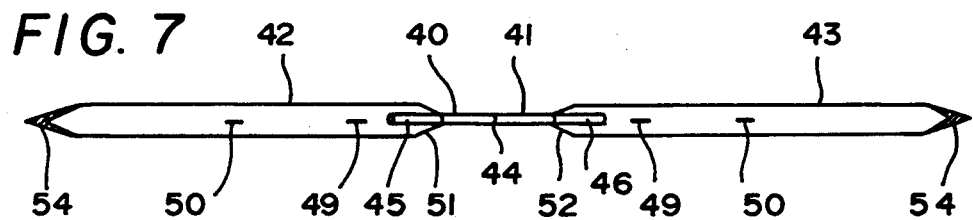
FIG. 7
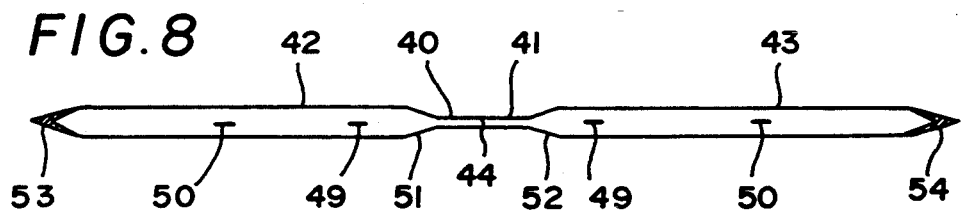
FIG. 8

APPARATUS FOR INTUBATION OF LACRIMAL DRAINAGE PATHWAY

FIELD OF THE INVENTION

This invention relates to an apparatus for intubation of lacrimal duct (lacrimal drainage pathway) for treatments of lacrimal duct obstruction and dry eye.

PRIOR ART

As shown in FIG. 1 the lacrimal duct consists of the upper punctum 11, lower punctum 12, upper canaliculus 13, lower canaliculus 14, common canaliculus 15, lacrimal sac 16 and nasolacrimal duct 17. The nasolacrimal duct 17 opens into the inferior nasal meatus in the nasal cavity. The length between the puncta and the lower end of the nasolacrimal duct is different from person to person and ranges between 33 and 45 mm (average 38 mm). For example, see Kurihashi et al: Int. Ophthalmol 15: 411–416, 1991. Any parts of obstruction in the lacrimal duct induce epiphora which annoy patients very much. On the other hand, dry eye is induced by deficiency of tears which are secreted from the lacrimal gland 19, resulting in feeling of dry sensation of the eyes, asthenopia, feeling of adhesion sensation and so on, which also put patients to annoyance as in epiphora. In conventional methods of treatment of lacrimal duct obstruction, major surgeries are performed with skin incision on the face to expose the bone surface of the frontal process of the maxilla, followed by creating the bony opening. On the other hand, as in previous methods of treatment of lacrimal duct obstruction, silicone intubation methods are also performed and its usefulness is confirmed. In silicone intubation methods, silicone tube is introduced into the lacrimal duct as a stent after probing to prevent reobstruction. The frontal process of the maxilla plays a role like a defensive wall for the ethmoid which is fragile and exists behind the maxilla. Major surgeries for the lacrimal duct obstruction create a big opening in the frontal process of the maxilla. Therefore, recently, the usefulness of the silicone intubation is enhanced. Japanese Patent Publication No. 56-50579 discloses the prior art John S. Crawford's method. As shown in FIGS. 2 and 3, probes 20, 21 as a guide are connected with both ends 22, 23 of silicone tube 24, 25, 26 and the probe 20 is introduced into the inferior nasal meatus from the lower punctum 12 via the lower canaliculus 14, common canaliculus 15, lacrimal sac 16, and nasolacrimal duct 17. The bulbous tip 27 of the probe is then caught by the hook 29 which is inserted from the nostril 18. The silicone tube 24 which is secured to it, is drawn into the lacrimal duct by pulling it from the inferior nasal meatus. In the same way, the other side 25 of the silicone tube is drawn into the lacrimal duct by pulling the bulbous tip 28 of the probe using the hook 29 to intubate as shown in FIG. 3. Both probes are removed and both sides 24, 25 of the silicone tube are fastened together in the nasal cavity as shown in FIG. 4. After silicone intubation the central part 26 of silicone tube appears between the upper and lower puncta. Other previous methods are similar in the point that silicone tube is drawn into the lacrimal duct by pulling probes from the inferior nasal meatus. For the treatment of dry eye, occlusion of the upper and lower puncta 11, 12 is performed by cautery to prevent tears from going to the lacrimal duct. After the occlusion by cautery, epiphora sometimes occurs. Therefore, recently, punctal plugs made from plastic materials are inserted into the puncta. Freemann's punctal plug (Freemann JM: Trans Am Acad Ophthalmol Otolaryngol 79: 874–879, 1975) is well known. If there is no problem caused by the punctal plug insertion, punctal occlusion by cautery is performed. In previous methods, probes must be pulled from the nostril, and this maneuver is the most difficult and during the procedure, epistaxis and bone fractures of the inferior nasal concha sometimes occur. It is not rare that it takes a lot of time to retrieve the probes from the nostril and the retrieval is impossible. Especially, in babies, it is very difficult to retrieve the probe from the nostril for the treatment of the lacrimal duct obstruction. Previous silicone tubes are uniforme in thickness in its total length, and because of its elasticity, the silicone tubes cannot form a narrow U-shape. Therefore, silicone tube is not stable in the lacrimal duct and it is not rare that the silicone tube migrates from the puncta after intubation. In prior arts, both ends of silicone tube which are inserted from the upper and lower puncta are fastened in the nasal cavity making knots, and if a naughty child applies traction to the exposed tube, retrograde migration of the knots 30 into the lacrimal sac 16 occurs as in FIG. 5, resulting in difficulty of removing the tube.

Kraft et al (Kraft et al: Am. J. Ophthalmol 94:290–298, 1982) and Psilas et al (Psilas et al: Dacriology News No. 1: 25, 1992) reported high success rates of silicone intubation by conventional methods for lacrimal duct obstruction which are 80.3% and 78% respectively. However, generally, major surgical interventions such as dacryocystorhinostomy are performed immediately without resorting to silicone intubation. The reason is based on the fact that it is very difficult to retrieve probe from the inferior nasal meatus in conventional silicone intubation methods. If there is a simple silicone intubation method without the difficult nasal procedure, all doctors will do silicone intubation before resorting to major surgical interventions, and many patients will be cured only by the silicone intubation, resulting in avoidance of major surgeries. For treatment of dry eye, punctal plug insertion is performed. However, there is a problem. The plug tends to come out because of its shallow insertion.

SUMMARY OF THE INVENTION

In the apparatus for intubation of the present invention, one or both end(s) of the silicone tube is sharp pointed and closed. Preferably, the central part of the silicone tube is thinner. In desirable state of this invention, the apparatus for intubation of lacrimal duct consists of a prescribed length of soft tube to intubate into the lacrimal duct and a pair of probes which are inserted into both sides of tube from a small cut, and both ends of tube are sharp pointed and closed and the tube consists of the central, thinner and softer tube or rod, and bilateral thicker and harder tubes. It is desirable that the middle point of the central segment of the tube is marked. A pair of probes are introduced into the bilateral thicker and harder segments till both tips of the tube from the small cuts which are made parallel to the segments. Both ends of the tube are sharp pointed in conical shape and closed. Jointed portions of the central thinner segment with the bilateral thicker segments are a gentle slope. In another state of the present invention, the intubation apparatus is one piece tube which consists of the central thinner and softer tube or rod and the bilateral thicker and harder tubes without any connected joints, and both ends are sharp pointed in conical shape and closed. A tube which consists of only the thicker and harder tube with a sharp pointed tip in conical shape can be made.

A tube which consists of only the thicker and harder tube or rod with a sharp pointed tip in conical shape and with the other bulbous tip like bulbous tip of a match can be made.

ADVANTAGES OF THE INVENTION

Unlike prior arts, the apparatus for intubation according to the present invention, does not require difficult nasal procedure at all, resulting in short operating time and a small burden on patients. The central segment of tube in the present invention is thinner and softer. Therefore, the tube can form a narrow U-shape which makes the tube stable in the lacrimal duct without easy migration. Because patients feel small pains, it is easy to do reoperation if the first operation ends in failure. Because no knot of silicone tube in the nasal cavity is required, there is no problem of retrograde migration into the lacrimal sac, resulting in no difficulty in removal if migration should occur. Although, it is easy to insert the apparatus for intubation of the present invention into the lacrimal duct and easy to remove it, it is not easily dislocated during intubation period. If the middle point of the central thinner segment of the present invention is marked, it is easy to confirm if the tube is intubated correctly or not. One piece tube without any connected joints is better because there is no anxiety for the joints to come off. Gentle changeovers between the thicker segments and thinner segment of the tube, reduce stimulation to the cornea by the cut edges of the thicker tube if migration should occur.

The small cuts applied parallel to the thicker tube do not break the tube. Furthermore, the tube with sharp pointed tips in conical shape can be easily intubated into the lacrimal duct from the puncta after punctal dilation with the punctal dilator only without punctal incision.

Using this tube, intubation into the lacrimal duct can be performed more easily.

This fact makes doctors possible to do intubation routinely before resorting to major surgical interventions and 60 to 80% of patients are considered to be cured by this simple treatment, without resorting to major surgeries. This is a big help to patients with lacrimal obstruction. Furthermore, the present invention resembling a nunchaku can be used for patients with dry eye. The nunchaku-style tube is not easily dislocated compared to punctal plug.

BRIEF DESCRIPTION OF THE DRAWINGS

FIG. 4 is a schematic diagram showing the method of the prior art.

FIG. 5 is a schematic diagram showing a problem in the prior art.

FIG. 6 is a lateral view showing the apparatus for intubation of the present invention.

FIG. 7 is a lateral view showing the apparatus for intubation of the apparatus for intubation of the present invention.

FIG. 8 is a lateral view showing the apparatus for intubation of the present invention.

DESCRIPTION OF THE PREFERRED EMBODIMENTS

The procedures of intubation by the first embodiments using the present invention will be explained. The apparatus for intubation shown in FIGS. 6, 7 and 8 is a 50 to 120 mm silicone tube which consists of the central thinner and softer segment 20 to 40 mm in length and the bilateral thicker and harder ends and both ends of the silicone tube are sharp pointed and closed. Thus, the tube resembling nunchaku which is used by Chinese martial art practitioners, has been discovered as the present invention which suits the purpose mentioned above.

The nunchaku consists of two wooden sticks connected each other by a chain.

Plastic tube used in the present invention should be substantially unstimulating and nontoxic to a living body. From this point of view, safety of silicone tube is established. So silicone tube is appropriate and above all the combination of silicone tube 0.9–1.2 mm OD and 0.5–0.7 mm ID with that 0.5–0.7 mm OD and 0.3–0.5 mm ID is most preferably used.

Figure 9:
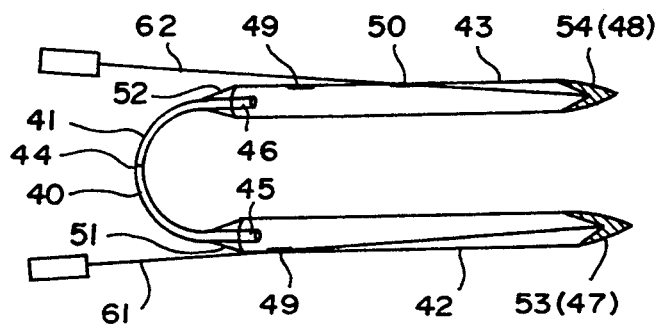
FIG. 9 is a perspective view showing the state of the apparatus for intubation of the present invention at the time of operation.
Figure 10:
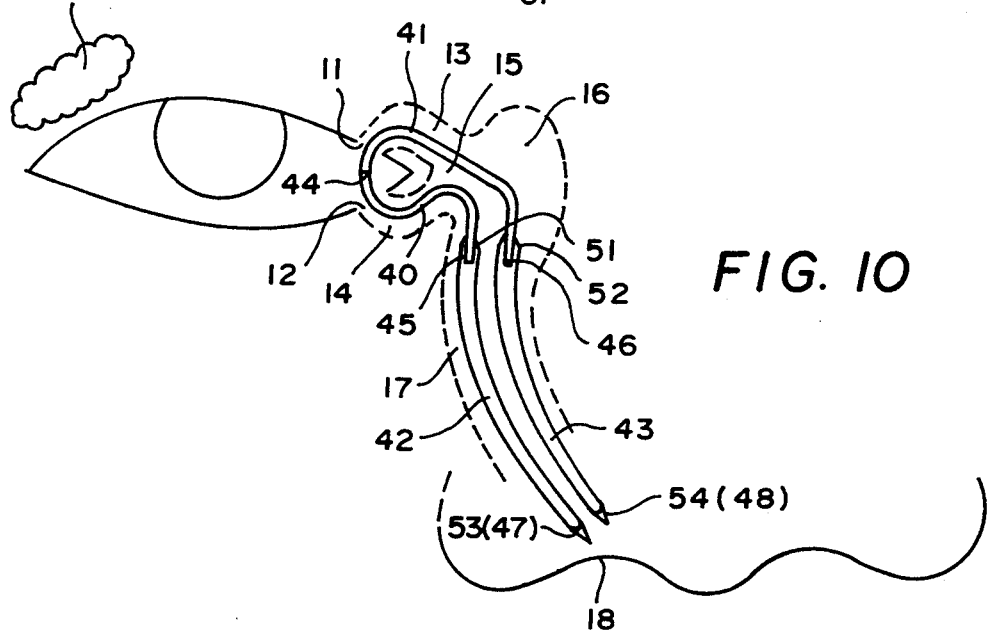
FIG. 10 is a schematic diagram showing the method of intubation using the apparatus for intubation of the present invention.

As shown in FIGS. 8, 9 and 10, both sides 40, 41 of the thinner tube (0.5–0.7 mm OD, 0.3–0.5 mm ID and 20–40 mm in length) are connected with the thicker tubes (0.9–1.2 mm OD, 0.5–0.7 mm ID and 15–50 mm in length) 42, 43.

The tube 42 and tube 43 are almost same in length.

Two millimeter ends of the thinner tube are inserted into the thicker tube for connection. Therefore, the jointed portions 45, 46 are 2 mm in length and fixed by silicone glue. The tips 47, 48 of the thicker tubes are sharp pointed and closed. To close 2 mm ends of the tubes, rod of the same diameter with the inner diameter of the tubes is inserted into the tubes with silastic adhesive. Thus, the inner space of the 2 mm tips of the tube are completely sealed with silicone, and diagonally cut to taper the closed ends 47, 48.

Small cuts 0.5 mm in length 49, 50 for probes 0.4 mm in diameter to insert, are applied to the thicker tubes parallel to the tubes. If the small cuts are applied perpendicularly to the tubes, the tubes may be broken during operation. The positions of the small cuts are 10 to 45 mm from the tips of the thicker tubes and one small cut existing at the middle point 50 and another one close to the joints 49 make intubation into the lacrimal duct easier using probe inserted from these small cuts. Markings corresponding to the positions of the small cuts make it easier to discover the small cuts. Thus, a total length of 50–120 mm tube is made.

If the central thinner tube is 25–40 mm, the bilateral thicker tube should be 15–30 mm in length for easy intubation, resulting in a total length of 70–100 mm. The total length of the tube is 100–120 mm for adults and 70–100 mm for children.

The length and thickness of the tube depend on length of the lacrimal duct and size of the inner space of the individual lacrimal ducts. The present invention 105 mm in total length which consists of the central thinner segment 0.64 mm in thickness and 25 mm in length, and bilateral thicker segment, 0.94 mm in thickness and 40 mm in length is most frequently used. For the treatment of dry eye, two thinner present inventions or one thicker present invention are used effectively.

In order for the tube to be stable in the lacrimal duct, it is important that the central segment of the tube is thinner and softer. Not only the tube 0.5–0.7 mm OD above mentioned, but also rod 0.5–0.7 mm in diameter without inner space is useful for the central segment.

The middle point 44 of the central thinner segment is marked. It is good for this marking to mark itself or tie around the middle point of tube with a 9-0 nylon. The central thinner segment is transparent or white, and the bilateral thicker segments must be transparent to be able to see the position of the probe inserted into it.

The mark 44 in the middle point of the central thinner segment makes it possible to see if the tube is correctly positioned or not. If it is correctly inserted, the mark 44 exists between the upper and lower puncta. If it is not correctly inserted, the mark 44 is invisible. Once the tube is correctly inserted, migration of the tube is rare. If migration of the tube should occur, and the step-like junctions 44, 46 appear between the upper and lower puncta, patient will feel ocular pain by stimulation of the cut edge of the thicker tube at the junctions with the central thinner segment. As shown in FIG. 7, it is better to make slopes 51, 52 without making any steps at the junction in order not to stimulate the cornea. The slope 51, 52 can be made by spreading silicone glue on the step.

As shown in FIG. 7, if both ends 53, 54 of the present invention are sharp pointed in conical shape, it is more easily inserted from the lacrimal puncta.

It is very rare that the junctions 45, 46 come off. However, as shown in FIG. 8, one piece tube without any junctions which consists of the central thinner segments 40, 41 of tube or rod and the bilateral thicker segments 42, 43 of tube is best.

In FIG. 8, both ends 53, 54 are sharp pointed in conical shape and closed, and the junctions 51, 52 between the thinner and thicker segments are gentle slope without making any steps as shown in FIG. 7.

Figure 11:
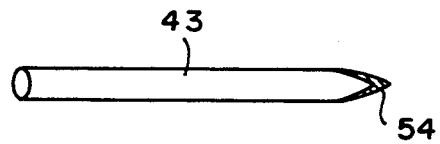
FIG. 11 is a lateral view of the apparatus for intubation of the present invention.
Figure 13:
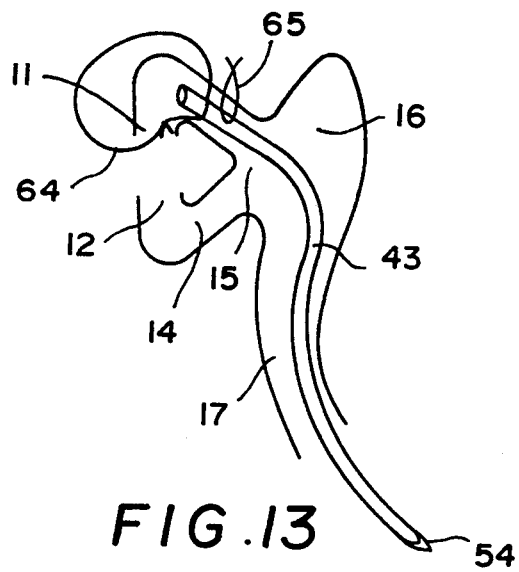
FIG. 13 is a schematic diagram showing the method of intubation using the apparatus for intubation of the present invention.

As shown in FIG. 9, the tube equipped with probes in advance is more convenient. As shown in FIG. 10, the above nunchaku style structure is suitable for intubation into the lacrimal duct from the upper and lower puncta. As shown in FIG. 13, intubation from the upper punctum (or lower punctum) is also an useful method for the treatment of lacrimal duct obstruction. In this method, as shown in FIG. 11, the thicker segment 43 only shown in FIGS. 7 and 8 is used and the tip 54 is similarly sharp pointed in conical shape and closed.

When it is inserted from the upper punctum 11, the probe 63 is inserted into the tube 43 till the tip 54 and the tube 43 enclosing the probe 63 is introduced into the lacrimal duct.

Figure 14:
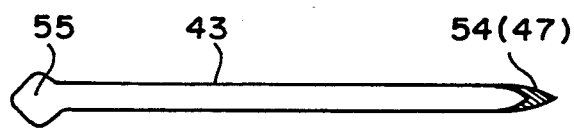
FIG. 14 is a lateral view of the apparatus for intubation of the present invention.
Figure 15:
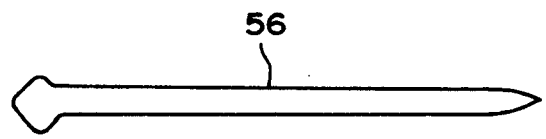
FIG. 15 is a lateral view of the apparatus for intubation of the present invention.
Figure 16:
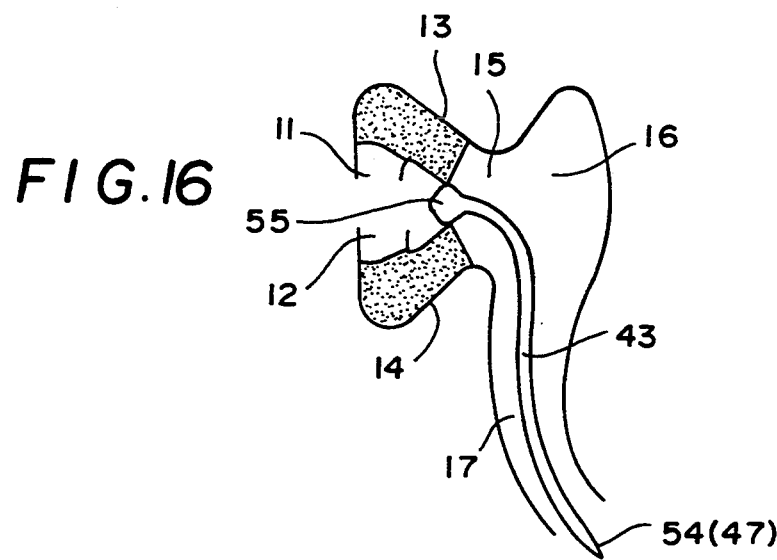
FIG. 16 is a lateral view of the apparatus for intubation of the present invention.

After the tube is inserted, only the probe 63 is removed and the end of the tube is fixated with 7-0 nylon thread 64, 65 (FIG. 13). If the upper and lower canaliculi 13, 14 are cicatrized as shown in FIG. 16, the common canaliculus 15 is opened and silicone tubes or rod as shown in FIGS. 14, 15 and 16 looking like a match with bulbous tip are inserted. The tube in this style is made from the thicker segment of the above mentioned apparatus and one end 47 is closed and the other end 55 is bulbous like a match. As shown in FIG. 14, the tube with the sharp pointed in conical shape and closed tip 54 is also excellent. Rod 56 with the same style in which one end is sharp pointed and the other end is bulbous is also useful (FIG. 15).

All the present inventions are used under local or general anesthesia using an operating microscope and can be simply carried out for almost all patients under local anesthesia. First of all, intubation method of the present invention will be explained using FIGS. 6, 7, 8, 9 and 10 as follows.

One closed end (47 or 53) of the tube is inserted from the lower punctum 12. Like previous methods, before the insertion of the tube, obstructed segment(s) of the lacrimal duct is opened by insertion of probe. As in the previous methods, the puncta are dilated by punctal incision at their lateral wall or using a punctal dilator.

As shown in FIG. 9, one end (47 or 53) of the tube 40, 42 enclosing the probe 0.4 mm in diameter 61 introduced from the small cut 49 applied to the thicker tube till the tip (47 or 53) of the tube 42 is pushed into the inferior nasal meatus from the lower punctum from the lower punctum 12 via the lower canaliculus 14, common canaliculus 15, lacrimal sac 16 and nasolacrimal duct 17.

FIG. 10 shows the post operative state of the present invention inserted into the lacrimal duct, and the mark 44 at the middle point of the central thinner tube 40, 41 of the present invention appears between the upper and lower puncta. As above mentioned, there is no difficult procedure in the nasal cavity with the present invention. Silicone tube can be placed in the lacrimal duct for a long time because it is unstimulating and nontoxic to a living body. The present invention can be easily removed by pulling the middle point 44 of the central thinner segment which appears between the upper punctum 11 and lower punctum 11 using forceps.

Figure 12:
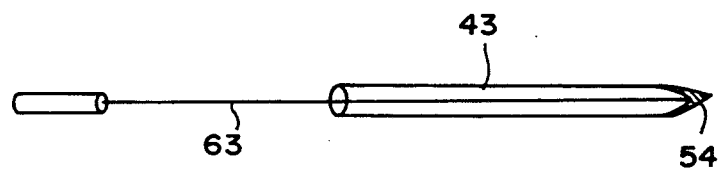
FIG. 12 is a perspective view showing the state of the apparatus for intubation of the present invention at the time of operation.

The intubation method using another apparatus for intubation will be explained as follows (FIGS. 11, 12 and 13).

As shown in FIG. 12, the tube 43 enclosing the probe 63 inserted into it till the closed end 54 which is sharp pointed in conical shape is introduced into the lacrimal duct from the upper punctum 11 to the inferior nasal meatus via the upper canaliculus 13, common canaliculus 15, lacrimal sac 16, nasolacrimal duct 17 as in FIG. 13. After this, the other end of the tube is fixated at the upper punctum and the upper canaliculus with 7-0 nylon to prevent dislocation of the tube. One side of the 7-0 nylon secured to the other end of the tube is drawn out from the upper punctum, and the other side of the 7-0 nylon is drawn out penetrating through the upper canaliculus. Both sides of the 7-0 nylon is then fastened together making a knot 64 in order not to be outside the punctum.

By pulling the 7-0 nylon, the tube can be removed from the upper punctum 11. The fixation by the 7-0 nylon only is not sufficient to fixate the tube, so both sides of one more 7-0 nylon penetrating through the tube enter through the upper canaliculus and both sides are fastened together making a knot which exists on the surface of skin at the most medial portion of the upper lid.

In the same way, the method in which the tube 43 is placed in the lacrimal duct from the lower punctum 12 and fixated using 7-0 nylon is also useful, but the method intubated from the upper punctum is easier.

Next, the method of other embodiment will be explained using FIGS. 14–16. As shown in FIG. 16, in cases with the upper 13 and lower 14 canalicular obstruction with cicatrices, the method is used to give life to the remaining common canaliculus 15. Under an operating microscope, the opening of the common canaliculus 15 is exposed and the tube or rod shown in FIGS. 14, 15 and 16 is introduced from the opening of the common canaliculus. As the other end is bulbous like a match, the tube or rod does not dislocate. Therefore it is easy to remove it. It has been confirmed by the inventor in plural cases that tears flow into the lacrimal duct by creating the opening of the remaining common canaliculus.

If all of the canalicular system are obstructed, the opening of the lacrimal sac is exposed in the same way and the tube resembling a match is introduced from it. The thicker silicone tube 1.75 mm OD resembling a match as shown in FIGS. 14, 15 and 16 is also useful. In the present invention, the tube can form a U-shape because it consists of the central thinner and softer tube or rod, and bilateral thicker and harder tube. Therefore, it is stable in the lacrimal duct.

Furthermore, the tube can be surely introduced into the lacrimal duct by probe inserting into it because the tips of the tube are closed.

Figure 17:
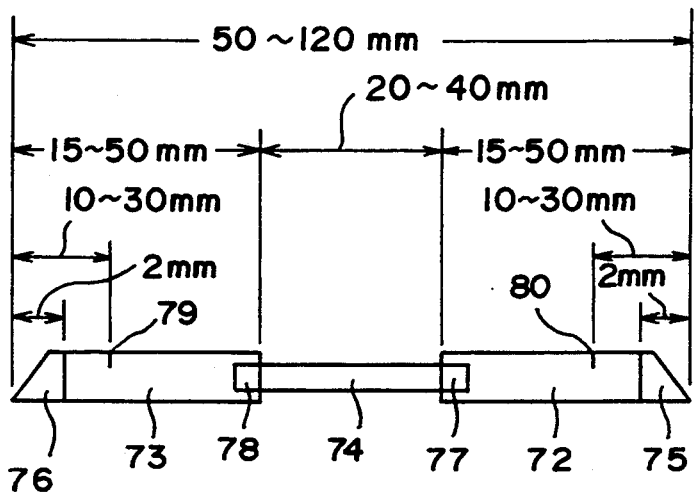
FIG. 17 is a schematic lateral view showing another method using the apparatus for intubation of the present invention.

Furthermore, other embodiments will be explained. As shown in FIG. 17, silicone tube 50–120 mm in length in which the central segment 20–40 mm is thinner and softer and both ends are sharp pointed and closed, is used as an apparatus to treat lacrimal duct obstruction(s). Regarding plastic tube for the embodiments in FIG. 17, it is important to select one which is substantially unstimulating and non-toxic to the tissue of the eye and a living body.

From this point of view, silicone tube is appropriate because its safety is already established as a apparatus for treatment of lacrimal duct obstruction, and above all, the combination of silicone tube 0.9~1.2 mm OD and 0.5–0.7 mm ID with that 0.5–0.7 mm OD and 0.3–0.5 mm ID is especially preferably used.

Its structure will be explained. As shown in FIG. 17, both sides of a thinner silicone tube 74, 0.5–0.7 mm OD, 0.3–0.5 mm ID and 20–40 mm in length are connected with bilateral thicker tubes 72, 73, 0. 9–1.2 mm OD, 0.3–0.5 mm ID and 15–50 mm in length. Silicone tube 72 and silicone tube 73 are same in length. Two millimeter ends of the thinner tube are inserted into the thicker tube for connection. Therefore, the jointed portions 77, 78 are 2 mm in length and the portions are fixed by silicone glue.

The tips 75, 76 of the thicker silicone tube are sharp pointed and closed, that is, rod in same diameter with the inner diameter of the silicone tubes, is inserted into 2 mm tip of the tubes with silicone glue. Thus, the inner space of the 2 mm ends of the tube are completely sealed with silicone, and diagonally cut to taper the tips to make the sharp pointed and closed ends 75, 76. To insert a metal probe 0.4 mm or less in diameter into the thicker tube, small cuts 79, 80 are applied. The position of the small cuts are 10 to 30 mm from the tips of the thicker tubes. Thus, a total length of 50–120 mm silicone tube is made. If the central thinner segment is 25–40 mm, the bilateral thicker tube should be 15–30 mm in length, resulting in a total length of 70–100 mm.

Regarding the total length of the present invention, 100–120 mm ones are appropriate for adult-nasolacrimal duct obstruction and 70~100 mm ones for child-nasolacrimal duct obstruction. The length and thickness of the silicone tube depend on length and size of the inner space of the individual lacrimal ducts.

A total length of 50–100 mm is appropriate for canalicular obstruction in adults and children. For children, thinner ones are used. In the embodiment shown in FIG. 17, in order to be stable in the lacrimal duct, it is important that the central segment of the silicone tube is thinner and softer, and not only silicone tube 0.5–0.7 mm OD above mentioned but also soft rod 0.5–0.7 mm in diameter without inner space is useful for making the central segment.

The embodiment in FIG. 17, is preferably used under local or general anesthesia, and one closed end of silicone tube is introduced from the lower punctum 12. Like previous methods, before insertion of the tube, obstructed portion(s) of the lacrimal duct is opened by insertion of probe(s) (a thin metal stick). Like previous methods, to dilate of the opening of the puncta, incision of the lateral wall of punctum and/or insertion of a punctal dilator is performed in advance.

Figure 18:
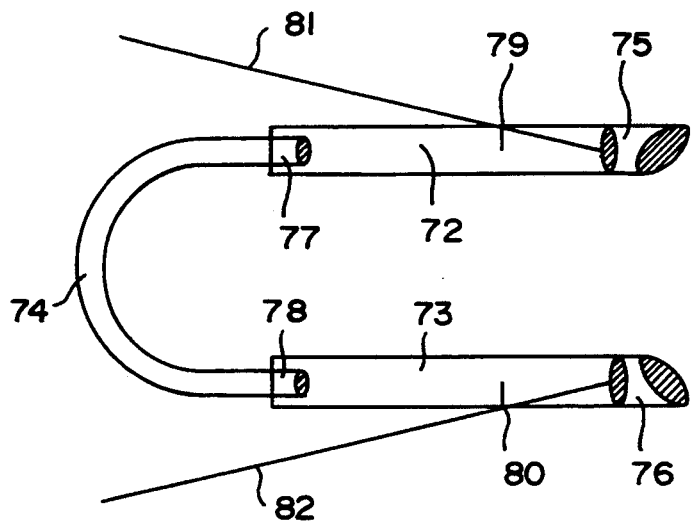
FIG. 18 is a perspective view showing the state of the apparatus shown in FIG. 17 at the time of operation.

As shown in FIG. 18, silicone tube 72 enclosing probe 81 ex. metal probe 0.4 mm or less in diameter which is inserted into the thicker silicone tube from a small cut of the silicone tube till the tip 75, is introduced into the nasal cavity (the inferior nasal meatus) from the lower punctum via the lower canaliculus, lacrimal sac and nasolacrimal duct.

After this only the probe 8 is then removed and silicone tube 72 is left in place. Next, the other side of silicone tube 73 is inserted from the upper punctum 11, and before the insertion a probe 1 mm in diameter (metal probe) is inserted from the upper punctum 11. The upper punctum is also dilated by incision of lateral wall of the punctum and/or insertion of punctal dilator. Silicone tube 73 enclosing probe 82 which is inserted into the thicker silicone tube from a small cut 80 at the middle point of the thicker silicone tube, is pushed into the nasal cavity (the inferior nasal meatus) from the upper punctum via the upper canaliculus, lacrimal sac and nasolacrimal duct in the same way.

Figure 19:
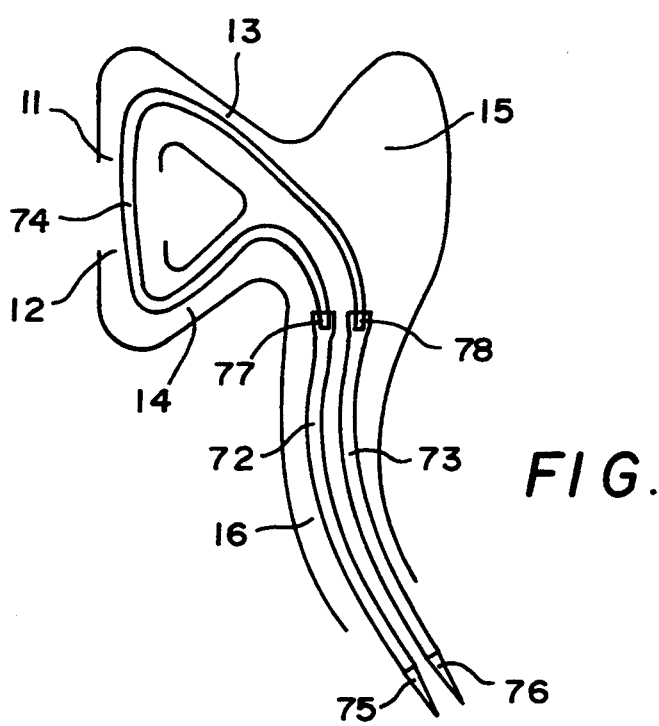
FIG. 19 is a schematic diagram showing the method using the intubation method indicated by FIG. 17.

FIG. 19 shows the postoperative state of the placement of the apparatus of the present invention, and the central part of silicone tube 74 appears between the upper punctum 11 and lower punctum 12.

Because the silicone tube is unstimulating and non-toxic to a living body, it can be left in place for a long time. Silicone tube can be easily removed by pulling the central part of the thinner silicone tube 74 which appears between the upper punctum 11 and lower punctum 12 using forceps. Central part of silicone tube is thinner and softer, so silicone tube can form a narrow U-shape, resulting in being stable in the lacrimal duct. Furthermore, silicone tube can be surely pushed into the lacrimal duct because the tip of silicone tube is closed.

Next, cases No. 1-3 treated successfully by the embodiment in FIG. 17 will be shown.

Case No. 1

Upper and lower canalicular obstructions in the right side. Main complaint of severe epiphora during the past 20 years. With severe epiphora, the right eye is blurred occasionally. The present invention was applied to the patient. On the 2nd postoperative day, epiphora began to decrease. On the 6th postoperative day, it became normal in spite of existence of silicone tube. On the 13th postoperative day, silicone tube was removed. But during the past days, silicone tube did not come out. Four months after the operation, patency of the lacrimal duct was gained and the lacrimal state was completely normal.

Case No. 2

Nasolacrimal duct obstruction in the left side. On the 7th postoperative day after performing the present invention, silicone tube was removed. The following day after the removal, epiphora disappeared. On the 144th postoperative day, epiphora completely disappeared.

Case No. 3

Nasolacrimal duct obstruction in the right side. The present invention was applied. After removing the silicone tube, the lacrimal duct was reobstructed and epiphora reoccured. Silicone intubation was performed again in the same way. On the 2nd postoperative day epiphora decreased conspicuously resulting in complete healing at the present time.

Next, cases No. 4-6 treated successfully by the silicone tubes of the present invention (FIGS. 6-16) will be explained.

Case No. 4

A child with nasolacrimal duct obstruction in the right side. The child was unsuccessfully treated by several other hospitals. Silicone tube as in FIG. 13 was quickly inserted and removed 2 weeks after the operation, resulting in good success.

Case No. 5

A young adult man with upper and lower canalicular obstruction in the left side. Because of severe epiphora, he got unsound mind and decreased desire for labour. The opening of the common canaliculus was made and from it, silicone tube as in FIG. 15 was inserted. Three months after the operation, the new opening for the lacrimal duct was created and epiphora decreased conspicuously, resulting in having sound mind and desire for labour.

Case No. 6

Dry eye. Intubation of nunchaku style silicone tube as in FIG. 6 was carried out. The following day, tear accumulation was observed in the right eye, and feeling of dryness in the right eye decreased.

Out of 31 adult-nasolacrimal duct obstructions, 18 (58.1%) was successfully treated by the nunchaku style silicone tube of the present invention. Out of 8 adult-canalicular obstructions, 100 % of success rate was gained by the nunchaku style silicone.

Out of 2 cases with canalicular and nasolacrimal duct obstructions, one case (50% ) was successful. Therefore, out of 41 cases, 27 (65.9%) was successful and the patients with success escaped major surgical interventions.

I claim:

1. A device for intubation of the lacrimal duct comprising:
    a flexible tube having a pair of cuts permitting insertion of probes, said flexible tube having a length of 50–120 mm, said flexible tube including a central, thinner soft segment and a pair of tubular segments depending from the ends of said soft segment, each of said tubular segments having an outside diameter significantly larger than the outside diameter of said soft segment, and having a free end which is sharp-pointed and sealed closed.

2. The device of claim 1 wherein the exterior of said length of flexible tube includes sloping surface portions joining said soft segment with said tubular segments, each of said sloping surface portions presenting a smooth tapered surface extending from the outer circumference of one of said tubular segments onto the surface of said soft segment.

3. The device of claim 2 wherein each of said sloping surface portions is formed of a silicone glue applied around an end of said soft segment and abutting an end of a tubular segment.

4. The device of claim 3 wherein said flexible tube is a total length of 50–100 mm.

5. The device of claim 1 wherein the center of said length of flexible tube is marked.

6. The device of claim 1 wherein said small cuts run parallel to the length of the flexible tube.

7. The device of claim 1 wherein said free ends have a conical shape.

8. The device of claim 1 wherein said length of flexible tube, inclusive of said thinner soft segment and said harder tubular segments has a unitary, single-piece construction.

9. The device of claim 1 wherein each of said tubular segments is less flexible than said soft segment.

10. The device of claim 1 wherein said soft segment has a length of 20–40 mm and each of said tubular segments has a length of 15–50 mm.

11. The device of claim 1 wherein said soft segment is a solid rod.

12. The device of claim 1 wherein said soft segment is tubular.

13. The device of claim 1 wherein said length of flexible tube is made of silicone.

* * * * *

UNITED STATES PATENT AND TRADEMARK OFFICE
CERTIFICATE OF CORRECTION

PATENT NO. : 5,437,625
DATED : August 1, 1995
INVENTOR(S) : Kurihashi

It is certified that error appears in the above-identified patent and that said Letters Patent is hereby corrected as shown below:

Delete columns 1 through 10, and replaced with the columns, as shown on the attached pages.

Signed and Sealed this

Sixth Day of August, 1996

Attest:

BRUCE LEHMAN

*Attesting Officer*   *Commissioner of Patents and Trademarks*

APPARATUS FOR INTUBATION OF LACRIMAL DRAINAGE PATHWAY

FIELD OF THE INVENTION

This invention relates to an apparatus for intubation of lacrimal duct (lacrimal drainage pathway) for treatments of lacrimal duct obstruction and dry eye.

PRIOR ART

Figure 1:
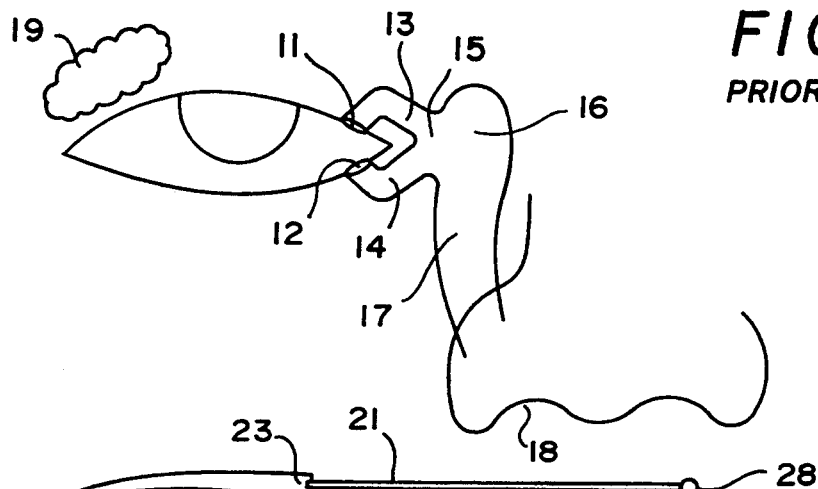
FIG. 1 is a schematic diagram of the lacrimal duct.
Figure 2:
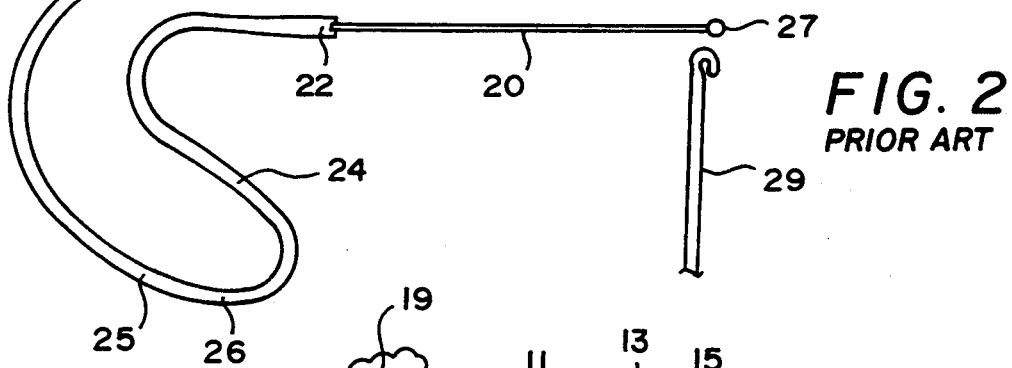
FIG. 2 is a schematic diagram of the prior art.
Figure 3:
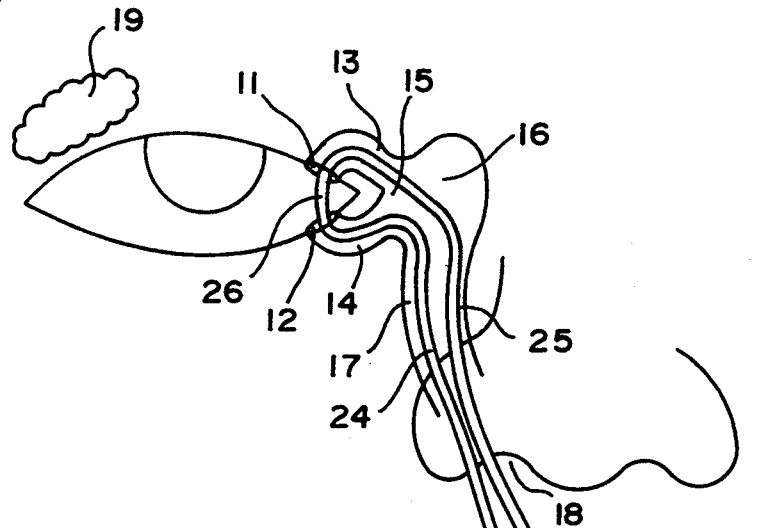
FIG. 3 is a schematic diagram showing the method of the prior art.

As shown in FIG. 1 the lacrimal duct consists of the upper punctum 11, lower punctum 12, upper canaliculus 13, lower canaliculus 14, common canaliculus 15, lacrimal sac 16 and nasolacrimal duct 17. The nasolacrimal duct 17 opens into the inferior nasal meatus in the nasal cavity. The length between the puncta and the lower end of the nasolacrimal duct is different from person to person and ranges between 33 and 45 mm (average 38 mm). For example, see Kurihashi et al: Int. Ophthalmol 15:411–416, 1991. Any obstruction in the lacrimal duct induces epiphora which annoys patients very much. On the other hand, dry eye is induced by deficiency of tears which are secreted from the lacrimal gland 19, resulting in feeling a dry sensation in the eyes, asthenopia, feeling of an adhesion sensation and so on, which are also annoyances as is epiphora. In conventional methods of treatment of lacrimal duct obstruction, major surgery is performed with skin incision on the face to expose the bone surface of the frontal process of the maxilla, followed by creating the bony opening. On the other hand, as in previous methods of treatment of lacrimal duct obstruction, silicone intubation methods are also performed and their usefulness has been confirmed. In silicone intubation methods, a silicone tube is introduced into the lacrimal duct as a stent after probing to prevent re-obstruction. The frontal process of the maxilla plays a role like a defensive wall for the ethmoid which is fragile and is located behind the maxilla. Major surgery for a lacrimal duct obstruction is undesirable in that it creates a big opening in the frontal process of the maxilla thus enhancing the usefulness of the silicone intubation method. Japanese Patent Publication No. 56-50579 discloses John S. Crawford's method which is shown as prior art in FIGS. 2 and 3. As shown in FIGS. 2 and 3, probes 20, 21 which serve as guides, are connected with respective ends 22, 23 of silicone tube 24, 25, 26. The probe 20 is introduced into the inferior nasal meatus from the lower punctum 12 via the lower canaliculus 14, common canaliculus 15, lacrimal sac 16, and nasolacrimal duct 17. The bulbous tip 27 of the probe is then caught by the hook 29 which is inserted through the nostril 18. The silicone tube 24 which is secured to it, is drawn into the lacrimal duct by pulling it from the inferior nasal meatus. In the same way, the other side 25 of the silicone tube is drawn into the lacrimal duct by pulling the bulbous tip 28 of the probe using the hook 29 to intubate as shown in FIG. 3. Both probes are removed and both sides 24, 25 of the silicone tube are fastened together in the nasal cavity as shown in FIG. 4. After silicone intubation the central part 26 of silicone tube appears between the upper and lower puncta. Other previous methods are similar in the point that a silicone tube is drawn into the lacrimal duct by pulling probes from the inferior nasal meatus. For the treatment of dry eye, occlusion of the upper and lower puncta 11, 12 is performed by cautery to prevent tears from going to the lacrimal duct. After the occlusion by cautery, epiphora sometimes occurs. Therefore, recently, punctal plugs made from plastic materials are inserted into the puncta. Freemann's punctal plug (Freemann JM: Trans Am Acad Ophthalmol Otolaryngol 79: 874–879, 1975) is well known. If there is no problem caused by the punctal plug insertion, punctal occlusion by cautery is performed. In previous methods, probes must be pulled from the nostril, and this maneuver is the most difficult and during the procedure, epistaxis and bone fractures of the inferior nasal concha sometimes occur. It is not rare that it takes a lot of time to retrieve the probes from the nostril or that the retrieval is impossible. Especially, in babies, it is very difficult to retrieve the probe from the nostril for the treatment of the lacrimal duct obstruction. Previous silicone tubes are uniform in thickness over their total length, and because of their elasticity, the silicone tubes cannot form a narrow U-shape. Therefore, a conventional silicone tube is not stable in the lacrimal duct and it is not rare that the silicone tube migrates from the puncta after intubation. In the prior art, both ends of silicone tube which extend through the upper and lower puncta are fastened in the nasal cavity by knotting, and if a child were to move the exposed tube, retrograde migration of the knots 30 into the lacrimal sac 16 could occur as in FIG. 5, resulting in difficulty of removing the tube.

Kraft et al (Kraft et al: Am. J. Ophthalmol 94: 290–298, 1982) and Psilas et al (Psilas et al: Dacriology News No. 1: 25, 1992) reported high success rates of silicone intubation by conventional methods for lacrimal duct obstruction which are 80.3% and 78% respectively. However, generally, major surgical interventions such as dacryocystorhinostomy are performed immediately without resorting to silicone intubation. The reason is based on the fact that it is very difficult to retrieve a probe from the inferior nasal meatus in conventional silicone intubation methods. Provision of a simple silicone intubation method without the difficult nasal procedure, would allow all doctors to perform a silicone intubation before resorting to major surgical intervention, and many patients would be cured merely by the silicone intubation, resulting in avoidance of major surgery. For treatment of dry eye, punctal plug insertion is performed. However, there is a problem in that the plug tends to come out because of the shallow depth of its insertion.

SUMMARY OF THE INVENTION

In the apparatus for intubation of the present invention, one or both end(s) of the silicone tube is sharp pointed and closed. Preferably, the central part of the silicone tube is thinner. In the preferred embodiments of this invention, the apparatus for intubation of the lacrimal duct consists of a prescribed length soft tube and a pair of probes which are inserted into both sides of the tube through a small cut. Both ends of the tube are sharp-pointed and closed and the tube consists of a central, thinner and softer tube or rod, and bilateral thicker and harder tubes. It is desirable that the middle point of the central segment of the tube be marked. A pair of probes are introduced into the bilateral thicker and harder segments until they abut respective tips of the tube, through the small cuts which are made parallel to the segments. Both ends of the tube are sharp-pointed, conical in shape and closed. Joints between the central thinner segment and the end thicker segments have a gentle slope. In another embodiment of the present invention, the intubation apparatus is a one piece tube which consists of the central thinner and softer tube or rod and the terminal thicker and harder tubes without any connecting joints. This latter embodiment also has both ends sharp-pointed, conical in shape and closed. A tube which consists of only the thicker and harder tube with a sharp pointed tip in conical shape can be made.

A tube which consists of only the thicker and harder tube or rod with one sharp-pointed tip in conical shape and with the other end bulbous, like the bulbous tip of a match, can be made.

Unlike prior art devices, the apparatus for intubation according to the present invention, does not require a difficult nasal procedure at all, thus enabling a short operating time and placing only a small burden on patients. The central segment of tube in the present invention is thinner and softer. Therefore, the tube can be formed into a narrow U-shape which makes the tube stable in the lacrimal duct without easy migration. Because patients feel small pain, it is easy to re-operate if the first operation ends in failure. Because no knotting of the silicone tube in the nasal cavity is required, there is no problem of retrograde migration into the lacrimal sac, thus avoiding the difficulty in removal if migration should occur. Although it is easy to insert the intubation device of the present invention into the lacrimal duct and easy to remove it, it is not easily dislocated during the intubation period. If the middle point of the central thinner segment of the present invention is marked, it is easy to confirm if the tube is intubated correctly or not. A one piece tube without any connecting joints is better because there is no danger of separation at the joints. Gentle transitions between the thicker segments and thinner segment of the tube, reduce stimulation of the cornea by the cut edges of the thicker tube if migration should occur.

The small cuts formed parallel in the thicker tube do not break the tube. Furthermore, the tube with sharp-pointed tips in conical shape can be easily intubated into the lacrimal duct from the puncta after punctal dilation with a punctal dilator only, without punctal incision.

Using this tube, intubation into the lacrimal duct can be performed more easily, which fact enables doctors to do intubations routinely, before resorting to major surgical interventions and 60 to 80% of patients are considered to be cured by this simple treatment, without resorting to major surgery. This is a big help to patients with lacrimal obstruction. Furthermore, the present invention resembling a nunchaku can be used for patients with dry eye. The nunchaku—style tube is not easily dislocated compared to the punctal plug.

BRIEF DESCRIPTION OF THE DRAWINGS

FIG. 1 is a schematic diagram of the lacrimal duct.
FIG. 2 is a schematic diagram of a prior art device.
FIG. 3 is a schematic diagram showing the method of the prior art.
FIG. 4 is a schematic diagram showing knotting in the method of the prior art.
FIG. 5 is a schematic diagram showing a problem in the prior art.
FIG. 6 is a lateral view showing an embodiment of the apparatus for intubation of the present invention.
FIG. 7 is a lateral view showing another embodiment of the apparatus for intubation of the apparatus for intubation of the present invention.
FIG. 8 is a lateral view showing yet another embodiment of the apparatus for intubation of the present invention.
FIG. 9 is a perspective view showing the state of the intubation device of the present invention at the time of operation.
FIG. 10 is a schematic diagram showing the method of intubation using the apparatus for intubation of the present invention.
FIG. 11 is a lateral view of another embodiment of the apparatus for intubation of the present invention.
FIG. 12 is a perspective view showing the state of the intubation device of the present invention at the time of operation.
FIG. 13 is a schematic diagram showing the method of intubation using the apparatus for intubation of the present invention.
FIG. 14 is a lateral view of another embodiment of the apparatus for intubation of the present invention.
FIG. 15 is a lateral view of the apparatus for intubation of the present invention.
FIG. 16 is a schematic diagram showing the intubation device of FIG. 14 in place.
FIG. 17 is a schematic lateral view showing the dimensions of another embodiment of an intubation device of the present invention.
FIG. 18 is a perspective view showing the state of the embodiment of FIG. 17 at the time of operation.
FIG. 19 is a schematic diagram showing the embodiment of FIG. 17 implanted in place.

DESCRIPTION OF THE PREFERRED EMBODIMENTS

The procedures of intubation using several embodiments of the present invention will be explained. The apparatus for intubation shown in FIGS. 6, 7 and 8 is a 50 to 120 mm tube which consists of the central thinner and softer segment 20 to 40 mm in length and thicker and harder end pieces which are sharp-pointed and closed. Thus, the tube of the present invention resembles a nunchaku, which is used by Chinese martial art practitioners.

The nunchaku consists of two wooden sticks connected to each other by a chain.

The plastic tube used in the present invention should be substantially non-stimulating and nontoxic to a living body. From this point of view, safety of silicone tube is established. So silicone tube is appropriate and a combination of a silicone tube 0.9–1.2 mm OD and 0.5–0.7 mm ID with silicone tubes 0.5–0.7 mm OD and 0.3–0.5 mm ID is most preferred.

As shown in FIGS. 8, 9 and 10, both sides 40, 41 of the thinner tube (0.5–0.7 mm OD, 0.3–0.5 mm ID and 20–40 mm in length) are connected with the thicker tubes (0.9–1.2 mm OD, 0.5–0.7 mm ID and 15–50 mm in length) 42, 43.

The tube 42 and tube 43 are almost the same in length. Two millimeter end lengths of the thinner tube are inserted into the thicker tube for connection. Therefore, the jointed portions 45, 46 are 2 mm in length and are fixed in place by silicone glue. The tips 47, 48 of the thicker tubes are sharp-pointed and closed. To close 2 mm end lengths of the tubes, rod of a diameter equal to the inner diameter of the tubes is inserted into the tubes with a silastic adhesive. Thus, the inner space of the 2 mm of the tips of the tube are completely sealed with silicone, and diagonally cut to taper the closed ends 47, 48.

Small cuts 0.5 mm in length 49, 50 for admitting probes 0.4 mm in diameter, are formed in the thicker tubes parallel to the tubes. If the small cuts are applied perpendicularly to the tubes, the tubes may be broken during operation. The positions of the small cuts are 10 to 45 mm from the tips of the thicker tubes and one small cut is provided at the middle point 50 and another one close to the joints 49 to make intubation into the lacrimal duct easier using probes inserted through these small cuts. Markings corresponding to the positions of the small cuts make it easier to locate the small cuts.

Thus, a tube having a total length of 50–120 mm is made.

If the central thinner tube is 25–40 mm, the end-piece thicker tubes should be 15–30 mm in length for easy intubation, resulting in a total length of 70–100 mm. The total length of the tube is 100–120 mm for adults and 70–100 mm for children.

The length and thickness of the tube depend on the length of the lacrimal duct and size of the inner space of the individual lacrimal ducts. A tube of the present invention having a total length of 105 mm, which consists of the central thinner segment 0.64 mm in thickness and 25 mm in length, and the terminal thicker segments, 0.94 mm in thickness and 40 mm in length, is most frequently used. For the treatment of dry eye, two thinner embodiments of the present invention or one thicker embodiment of the present invention are used effectively.

In order that the placement of the tube is stable in the lacrimal duct, it is important that the central segment of the tube is thinner and softer. Not only the tube 0.5–0.7 mm OD above mentioned, but also rod 0.5–0.7 mm in diameter without an interior passage is useful for the central segment.

The middle point 44 of the central thinner segment is marked. It is good for this marking to use a mark per se or to tie around the middle point of tube with a 9 - 0 nylon. The central thinner segment is transparent or white, and the end thicker segments must be transparent to enable the user to see the position of the probe inserted into it.

The mark 44 in the middle point of the central thinner segment makes it possible to see if the tube is correctly positioned or not. If it is correctly inserted, the mark 44 exists between the upper and lower puncta. If it is not correctly inserted, the mark 44 is invisible.

Once the tube is correctly inserted, displacement of the tube is rare. If displacement of the tube should occur, and the step-like junctions 45, 46 enter between the upper and lower puncta, the patient will feel ocular pain due to stimulation by the cut edge of the thicker tube at the junctions with the central thinner segment. As shown in FIG. 7, it is better to make slopes 51, 52, avoiding steps at the junctions in order not to stimulate the cornea. The sloped portions 51, 52 can be made by spreading silicone glue at the steps.

As shown in FIG. 7, if both ends 53, 54 of the device of the present invention are sharp-pointed and conical in shape, they are more easily inserted through the lacrimal puncta.

It is very rare that the junctions 45, 46 separate. However, as shown in FIG. 8, a one piece tube without any junctions which consists of the central thinner segments 40, 41 of tube or rod and the bilateral thicker segments 42, 43 of tube is best.

In FIG. 8, both ends 53, 54 are sharp-pointed, conical in shape and closed, and the junctions 51, 52 between the thinner and thicker segments are gently sloped without any steps as shown in FIG. 7.

As shown in FIG. 9, the tube equipped with probes in advance is more convenient. As shown in FIG. 10, the above nunchaku style structure is suitable for intubation into the lacrimal duct from the upper and lower puncta. As shown in FIG. 13, intubation from the upper punctum (or lower punctum) is also a useful method for the treatment of lacrimal duct obstruction. In this method, as shown in FIG. 11, the thicker segment 43 only, shown in FIGS. 7 and 8, is used and the tip 54 is similarly sharp-pointed, conical in shape and closed.

When it is inserted from the upper punctum 11, the probe 63 is inserted into the tube 43 up to the tip 54 and the tube 43 enclosing the probe 63 is introduced into the lacrimal duct.

After the tube is inserted, only the probe 63 is removed and the end of the tube is fixed with 7 - 0 nylon thread 64, 65 (FIG. 13). If the upper and lower canaliculi 13, 14 are cicatrized as shown in FIG. 16, the common canaliculus 15 is opened and silicone tubes or rod as shown in FIGS. 14, 15 and 16, looking like a match with a bulbous tip, are inserted. The tube in this style is made from the thicker segment of the previously described embodiments and one end 47 is closed and the other end 55 is bulbous like a match. As shown in FIG. 14, a tube with an end which has a sharp-pointed, conical in shape and closed tip 54 is also excellent. Rod 56 of the same style in which one end is sharp-pointed and the other end is bulbous is also useful (FIG. 15).

All of the embodiments of the present inventions are used under local or general anesthesia. Using an operating microscope the intubation operation can be simply carried out for almost all patients under local anesthesia.

The intubation method of the present invention will be explained with reference to FIGS. 6, 7, 8, 9 and 10 as follows.

One closed end (47 or 53) of the tube is inserted from the lower punctum 12. Like previous methods, before the insertion of the tube, obstructed segment(s) of the lacrimal duct are opened by insertion of probe. As in the previous methods, the puncta are dilated by punctal incision at their lateral wall or using a punctal dilator. As shown in FIG. 9, one end (47 or 53) of the tube 40, 42 enclosing the probe 0.4 mm in diameter 61 is introduced through the small cut 49 up to the tip (47 or 53) of the tube 42 and is pushed into the inferior nasal meatus from the lower punctum 12 via the lower canaliculus 14, common canaliculus 15, lacrimal sac 16 and nasolacrimal duct 17. FIG. 10 shows the post-operative state of the device of the present invention inserted into the lacrimal duct. The mark 44 at the middle point of the central thinner tube 40, 41 of the present invention appears between the upper and lower puncta. As mentioned above, there is no difficult procedure in the nasal cavity with the present invention. The silicone tube can remain in the lacrimal duct for a long time because it is non-stimulating and nontoxic to a living body. The device of the present invention can be easily removed by pulling the middle point 44 of the central thinner segment, which appears between the upper punctum 11 and lower punctum 11, using forceps.

The intubation method using another embodiment of the intubation device will be explained as follows (FIGS. 11, 12 and 13).

As shown in FIG. 12, the tube 43 enclosing the probe 63, inserted to the closed end 54 which is sharp-pointed and conical in shape is introduced into the lacrimal duct from the upper punctum 11 into the inferior nasal meatus via the upper canaliculus 13, common canaliculus 15, lacrimal sac 16, nasolacrimal duct 17 as in FIG. 13. After this, the other end of the tube is fixed at the upper punctum and the upper canaliculus with 7 - 0 nylon to prevent dislocation of the tube. One side of the 7 - 0 nylon secured to the other end of the tube is drawn out from the upper punctum, and the other side of the 7 - 0 nylon is drawn out penetrating through the upper canaliculus. Both sides of the 7 - 0 nylon are then fastened together making a knot 64.

By pulling the 7 - 0 nylon, the tube can be removed from the upper punctum 11. The fixation by the 7 - 0 nylon only is not sufficient to fix the tube, so both sides of one more 7 - 0 nylon penetrating through the tube enter through the upper canaliculus and both sides are fastened together by making a knot at the surface of skin at the most medial portion of the upper lid.

In the same way, the method in which the tube 43 is placed in the lacrimal duct from the lower punctum 12 and fixed in place using 7 - 0 nylon is also useful, but the method of intubation from the upper punctum is easier.

Next, a method using another embodiment of the device will be explained using FIGS. 14-16. As shown in FIG. 16, in cases with the upper 13 and lower 14 canalicular obstructed with cicatrices, the method is used to give life to the remaining common canaliculus 15. Under an operating microscope, the opening of the common canaliculus 15 is exposed and the tube or rod shown in FIGS. 14, 15 and 16 is introduced from the opening of the common canaliculus. As the other end is bulbous like a match, the tube or rod does not dislocate. Therefore it is easy to remove it. It has been confirmed by the inventor in plural cases that tears flow into the lacrimal duct by creating an opening in the remaining common canaliculus.

If all of the canalicular system is obstructed, the opening of the lacrimal sac is exposed in the same way and the tube resembling a match is introduced from it. The thicker silicone tube of 1.75 mm OD, resembling a match as shown in FIGS. 14, 15 and 16, is also useful. In the present invention, the tube can form a U-shape because it consists of the central thinner and softer tube or rod, and bilateral thicker and harder tube. Therefore, it is stable in the lacrimal duct.

Furthermore, the tube can be surely introduced into the lacrimal duct by a probe inserted into it because the tips of the tube are closed.

Furthermore, other embodiments will be explained. As shown in FIG. 17, a silicone tube 50-120 mm in length in which the central segment 20-40 mm is thinner and softer and both ends are sharp-pointed and closed, is used as an apparatus to treat lacrimal duct obstruction(s). Regarding the plastic tube used for the embodiment of FIG. 17, it is important to select one which is substantially non-stimulating and non-toxic to the tissue of the eye and a living body.

From this point of view, silicone is appropriate because its safety is already established in the treatment of lacrimal duct obstruction, and above all, the combination of silicone tube 0.9-1.2 mm OD and 0.5-0.7 mm ID with that 0.5-0.7 mm OD and 0.3-0.5 mm ID is especially preferred.

As shown in FIG. 17, both ends of a thinner silicone tube 74, 0.5-0.7 mm OD, 0.3-0.5 mm ID and 20-40 mm in length are connected with thicker tubes 72, 73, 0.9-1.2 mm OD, 0.3-0.5 mm ID and 15-50 mm in length. Silicone tube 72 and silicone tube 73 are the same in length. Two millimeter end portions of the thinner tube are inserted into the thicker tube for connection. Therefore, the jointed portions 77, 78 are 2 mm in length and the joints are fixed by silicone glue.

The tips 75, 76 of the thicker silicone tube are sharp-pointed and closed, that is, a rod of the same diameter as the inner diameter of the silicone tubes, is inserted into 2 mm of the tip of the tubes with silicone glue. Thus, the inner space of 2 mm of the ends of the tube are completely sealed with silicone, and diagonally cut to taper the tips to make the sharp-pointed and closed ends 75, 76. To insert a metal probe 0.4 mm or less in diameter into the thicker tube, small cuts 79, 80 are provided. The position of the small cuts are 10 to 30 mm from the tips of the thicker tubes. Thus, a total length of 50~120 mm silicone tube is made. If the central thinner segment is 25-40 mm, the end thicker tubes should be 15-30 mm in length, resulting in a total length of 70-100 mm.

Regarding the total length of the devices of the present invention, 100-120 mm is appropriate for adult-nasolacrimal duct obstruction and 70-100 mm is appropriate for child-nasolacrimal duct obstruction. The length and thickness of the silicone tube depend on the length and size of the inner space of the individual lacrimal ducts.

A total length of 50-100 mm is appropriate for canalicular obstruction in adults and children. For children, thinner ones are used. In the embodiment shown in FIG. 17, in order to remain stable in the lacrimal duct, it is important that the central segment of the silicone tube is thinner and softer. Not only the silicone tube 0.5-0.7 mm OD above mentioned but also soft rod 0.5-0.7 mm in diameter without interior space is useful for making the central segment.

The embodiment in FIG. 17 is preferably used under local or general anesthesia, and one closed end of the silicone tube is introduced from the lower punctum 12. As in previous methods, before insertion of the tube, obstructed portion(s) of the lacrimal duct are opened by insertion of probe(s) (a thin metal stick). As in previous methods, dilation of the opening of the puncta, incision of the lateral wall of punctum and/or insertion of a punctal dilator is performed in advance.

As shown in FIG. 18, the silicone tube 72 encloses a probe 81, e.g. a metal probe 0.4 mm or less in diameter, inserted into the thicker silicone tube through a small cut up to the tip 75. This assembly is introduced into the nasal cavity (the inferior nasal meatus) from the lower punctum via the lower canaliculus, lacrimal sac and nasolacrimal duct.

After this, the probe 8 only is then removed and silicone tube 72 is left in place. Next, the other side of silicone tube 73 is inserted from the upper punctum 11, after the prior insertion of a probe 1 mm in diameter (metal probe) from the upper punctum 11. The upper punctum is also dilated by incision of the lateral wall of the punctum and/or insertion of a punctal dilator. Silicone tube 73 enclosing probe 82 which is inserted into the thicker silicone tube through a small cut 80 at the middle point of the thicker silicone tube, is pushed into the nasal cavity (the inferior nasal meatus) from the upper punctum via the upper canaliculus, lacrimal sac and nasolacrimal duct in the same way.

FIG. 19 shows the postoperative state of the placement of the device of the present invention, and the central part of the silicone tube 74 appears between the upper punctum 11 and lower punctum 12.

Because the silicone tube is non-stimulating and non-toxic to a living body, it can be left in place for a long time. The silicone tube can be easily removed by pulling the central part of the thinner silicone tube 74 which appears between the upper punctum 11 and lower punctum 12 using forceps. The central part of the silicone tube is thinner and softer, so the silicone tube can form a narrow U-shape, resulting in stability in the lacrimal duct. Furthermore, the silicone tube can be reliably pushed into the lacrimal duct because the tip of silicone tube is closed.

Next, cases No. 1-13 treated successfully by the device of the embodiment in FIG. 17 will be described.

Case No. 1. Upper and lower canalicular obstructions in the right side. Main complaint was of severe epiphora over the past 20 years. With severe epiphora, the right eye is blurred occasionally. The device of the present invention was implanted in the patient. On the 2nd postoperative day, epiphora began to decrease. On the 6th postoperative day, it became normal in spite of the presence of the silicone tube. On the 13th postoperative day, the silicone tube was removed. But during the previous days, silicone tube did not come out. Four months after the operation, patency of the lacrimal duct was gained and the lacrimal state was completely normal.

Case No. 2. Nasolacrimal duct obstruction in the left side. On the 7th postoperative day after implantation of the device of the present invention, the silicone tube was removed. The following day after the removal, epiphora disappeared. On the 144th postoperative day, epiphora completely disappeared.

Case No. 3. Nasolacrimal duct obstruction in the right side. The present invention was applied. After removing the silicone tube, the lacrimal duct was re-obstructed and epiphora reoccurred. Silicone intubation was performed again in the same way. On the 2nd postoperative day epiphora decreased conspicuously resulting in complete healing at the present time.

Next, Cases No. 4-6 treated successfully by the silicone tubes of the present invention (FIGS. 6-16) will be described.

Case No. 4. A child with nasolacrimal duct obstruction in the right side. The child was unsuccessfully treated by several other hospitals. A silicone tube as shown in FIG. 13 was quickly inserted and removed 2 weeks after the operation, resulting in good success.

Case No. 5. A young adult man with upper and lower canalicular obstruction in the left side. Because of severe epiphora, he was unsound of mind and had a decreased desire for labor. The opening of the common canaliculus was made and through it, the silicone tube as in FIG. 15 was inserted. Three months after the operation, the new opening for the lacrimal duct was created and epiphora decreased conspicuously, resulting in sound mind and a desire for labor.

Case No. 6. Dry eye. Intubation of nunchaku style silicone tube as in FIG. 6 was carried out. The following day, tear accumulation was observed in the right eye, and the feeling of dryness in the right eye decreased.

Out of 31 adult—nasolacrimal duct obstructions, 18 (58.1%) were successfully treated by the nunchaku style silicone tube of the present invention. Out of 8 adult—canalicular obstructions, a 100% rate of success was gained by the nunchaku style silicone. Out of 2 cases with canalicular and nasolacrimal duct obstructions, one case (50%) was successful. Therefore, out of 41 cases, 27 (65.9%) were successful and the patients with success escaped major surgical interventions.

I claim:

1. A device for intubation of the lacrimal duct comprising:
a flexible tube having a pair of cuts permitting insertion of probes, said flexible tube having a length of 50-120 mm, said flexible tube including a central, thinner soft segment and a pair of tubular segments depending from the ends of said soft segment, each of said tubular segments having an outside diameter significantly larger than the outside diameter of said soft segment, and having a free end which is sharp-pointed and sealed closed.

2. The device of claim 1 wherein the exterior of said length of flexible tube includes sloping surface portions joining said soft segment with said tubular segments, each of said sloping surface portions presenting a smooth tapered surface extending from the outer circumference of one of said tubular segments onto the surface of said soft segment.

3. The device of claim 2 wherein each of said sloping surface portions is formed of a silicone glue applied around an end of said soft segment and abutting an end of a tubular segment.

4. The device of claim 3 wherein said flexible tube is a total length of 50-100 mm.

5. The device of claim 1 wherein the corner of said length of flexible tube is marked.

6. The device of claim 1 wherein said small cuts run parallel to the length of the flexible tube.

7. The device of claim 1 wherein said free ends have a conical shape.

8. The device of claim 1 wherein said length of flexible tube, inclusive of said thinner soft segment and said harder tubular segments has a unitary, single-piece construction.

9. The device of claim 1 wherein each of said tubular segments is less flexible than said soft segment.

10. The device of claim 1 wherein said soft segment has a length of 20-40 mm and each of said tubular segments has a length of 15-50 mm.

11. The device of claim 1 wherein said soft segment is a solid rod.

12. The device of claim 1 wherein said soft segment is tubular.

13. The device of claim 1 wherein said length of flexible tube is made of silicone.

* * * * *